US012653790B2

(12) United States Patent
Song et al.

(10) Patent No.: US 12,653,790 B2
(45) Date of Patent: Jun. 16, 2026

(54) PREPARATION METHOD OF AMISULPRIDE TABLET

(71) Applicant: HQ Pharma (Shandong) Co., Ltd., Shandong (CN)

(72) Inventors: Yijun Song, Shandong (CN); Xinmeng Cui, Shandong (CN); Dekai Chang, Shandong (CN)

(73) Assignee: HQ Pharma (Shandong) Co., Ltd., Shandong (CN)

( * ) Notice: Subject to any disclaimer, the term of this patent is extended or adjusted under 35 U.S.C. 154(b) by 355 days.

(21) Appl. No.: 18/339,972

(22) Filed: Jun. 22, 2023

(65) Prior Publication Data

US 2024/0165031 A1 May 23, 2024

(30) Foreign Application Priority Data

Nov. 18, 2022 (CN) .......................... 202211443501.8

(51) Int. Cl.
| | |
|---|---|
| *A61K 9/20* | (2006.01) |
| *A61K 31/40* | (2006.01) |
| *A61P 25/18* | (2006.01) |

(52) U.S. Cl.
CPC .......... *A61K 9/2081* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 31/40* (2013.01); *A61P 25/18* (2018.01)

(58) Field of Classification Search
CPC .. A61K 9/2081; A61K 9/2013; A61K 9/2018; A61K 9/2027; A61K 9/2054; A61K 9/2095; A61K 31/40; A61K 9/205; A61P 25/18
See application file for complete search history.

(56) References Cited

U.S. PATENT DOCUMENTS

2020/0383924 A1* 12/2020 Asada .................... A61K 47/38

FOREIGN PATENT DOCUMENTS

| | | |
|---|---|---|
| CN | 1842331 A | 10/2006 |
| CN | 111728947 A | 10/2020 |
| CN | 112535671 A | 3/2021 |

* cited by examiner

*Primary Examiner* — Sin J Lee
(74) *Attorney, Agent, or Firm* — Andrew M. Metrailer; Conley Rose, P.C.

(57) ABSTRACT

The present disclosure belongs to the technical field of medicine preparation, and provides a preparation method of an amisulpride tablet. The preparation method includes the following steps: coating amisulpride with a coating material, and then mixing a hydrophilic lubricant with obtained coated granules. In the present disclosure, a brand new solution is provided for a sticking problem caused by inherent properties of the amisulpride. The amisulpride is coated with a polymer coating material, and then the coated granules are mixed with a highly hydrophilic lubricant. The preparation method avoids easy sticking of the amisulpride. Meanwhile, the prepared amisulpride tablet has high hardness and desirable dissolution rate.

3 Claims, 2 Drawing Sheets

PREPARATION METHOD OF AMISULPRIDE TABLET

CROSS REFERENCE TO RELATED APPLICATION

This patent application claims the benefit and priority of Chinese Patent Application No. 2022114435018, filed with the China National Intellectual Property Administration on Nov. 18, 2022, the disclosure of which is incorporated by reference herein in its entirety as part of the present application.

TECHNICAL FIELD

The present disclosure relates to the technical field of medicine preparation, in particular to a preparation method of an amisulpride tablet.

BACKGROUND

Amisulpride is an atypical antipsychotic drug mainly used in the treatment of mental disorders. This drug is specifically used for the treatment of paranoid-like progressive schizophrenia and acute delirium-type mental disorders, and can also treat deficit states in schizophrenia, residual development of mental disorders, and suppressed states accompanied by bluntness. The drug is also useful in the treatment of prominent primary negative symptoms as well as psychotic depression.

Compressing is an essential process in the production of tablets for oral solid preparations. At present, in the production of amisulpride tablets, "sticking" is easy to occur during the compressing. The sticking may affect the properties of a plain tablet, and is more likely to seriously affect the weighting difference, resulting in unqualified content and content uniformity.

In the face of sticking, the current conventional solutions included:

(1) Change the dosage and type of lubricant: the dosage of lubricants such as magnesium stearate is increased and the type of magnesium stearate is changed. However, increasing the dosage of lubricants may result in a tablet with low hardness and slow disintegration time. Moreover, this measure may also affect the stability and dissolution profile of the product.

(2) Coating of a mold: the sticking may be relieved after the mold is coated. However, the coating is conducted with higher-cost materials such as Teflon and chrome. Moreover, during the production, this measure may cause the risk of coating shedding or abrasion, thereby reducing safety of the drug.

(3) Environmental control: an excessive ambient humidity during the compressing may cause sticking, such that the sticking can also be avoided through the environmental control. However, most of the sticking problems need to be avoided by controlling the ambient humidity below 35% RH, which puts extremely high demands on the air-conditioning system of the production workshop and increases energy consumption.

(4) Control of moisture and particle size distribution: the properties of blended granules may also cause sticking, such as the particle size distribution and moisture. However, the control of these factors can only take effect in most projects, and does not relieve the sticking caused by the inherent nature of some raw materials.

CN111728947A disclosed an amisulpride tablet and a preparation method thereof. The components of this amisulpride tablet include: amisulpride, a binder, a filler, a disintegrant, a lubricant, and an auxiliary lubricant. In this patent, when amisulpride tablets were prepared by a hot-melt method, it was unexpectedly found that the auxiliary lubricant was added to avoid sticking. The amisulpride tablet has a desirable dissolution rate at a pH value of 6.8, but shows poor hardness. This can lead to product fragmentation during packaging and shipping, affecting the product quality.

CN112535671A disclosed an amisulpride dispersible tablet and a preparation method thereof. In the preparation method, the active drug amisulpride is uniformly mixed with corresponding auxiliary materials, and wet granulation is conducted to obtain granules. The granules are coated with a fluidized bed, mixed with other auxiliary materials, and then compressed into a dispersible tablet. This patent avoids the sticking of amisulpride during the compressing, but the obtained dispersible tablet has poor hardness and low dissolution rate.

In the production of existing amisulpride tablets, to avoid sticking during the compressing, auxiliary lubricants or auxiliary materials are added. Although these measures solve the problem of sticking, the resulting tablets have poor hardness and low dissolution rate to varying degrees.

SUMMARY

In order to solve the above technical problems, an objective of the present disclosure is to provide a preparation method of an amisulpride tablet. The present disclosure solves the problem that the amisulpride is prone to sticking. Meanwhile, the prepared amisulpride tablet has high hardness and desirable dissolution rate.

To achieve the above objective, the present disclosure adopts the following technical solutions:

The present disclosure provides a preparation method of an amisulpride tablet, including the following steps: coating amisulpride with a coating material, and then mixing a hydrophilic lubricant with obtained coated granules.

Preferably, the coating material includes at least two selected from the group consisting of sodium alginate, povidone, ion exchange resin, ethyl cellulose, cellulose acetate, and hydroxypropyl cellulose; more preferably, the coating material includes the ethyl cellulose and the hydroxypropyl cellulose; and even more preferably, the ethyl cellulose and the hydroxypropyl cellulose are at a mass ratio of 1:1.

More preferably, the coating material is added at 1% to 3% of the weight of the amisulpride tablet.

Preferably, the hydrophilic lubricant is at least one selected from the group consisting of sodium stearyl fumarate, talcum powder, sodium lauryl sulfate, micronized silica gel, and polyethylene glycol, most preferably the sodium stearyl fumarate.

More preferably, the hydrophilic lubricant is added at 0.5% to 1.5% of the weight of the amisulpride tablet.

Preferably, before the amisulpride is coated, wet granulation is conducted on the amisulpride using the coating material to obtain wet granules.

Preferably, the preparation method of an amisulpride tablet specifically includes the following steps:

S1, wet granulation: conducting wet granulation on the amisulpride with the coating material to obtain wet granules;

S2, coating: subjecting the wet granules obtained in step S1 to coating, drying, and sieving to obtain coated granules;

S3, first mixing: mixing the coated granules obtained in step S2 with the hydrophilic lubricant to obtain a material 1;

S3, second mixing: adding an auxiliary material into the material 1 obtained in step S3, and mixing to obtain a material 2;

S4, total mixing: mixing the material 2 obtained in step S3 with a hydrophobic lubricant to obtain a total mixture; and S5, compressing: compressing the total mixture obtained in step S4 to obtain the amisulpride tablet.

Preferably, in step S1, the coating material accounts for 20% to 30% of a total mass of the coating material.

Preferably, in step S3, the auxiliary material does not have a lubricant.

More preferably, the auxiliary material includes at least one of a disintegrant, a filler, a sweetener, and a flavoring agent.

Preferably, in step S4, the hydrophobic lubricant accounts for 0.5% to 1.5% of the weight of the amisulpride tablet.

More preferably, the hydrophobic lubricant is at least one selected from the group consisting of magnesium stearate, calcium stearate, glycerol monostearate, and stearic acid, most preferably the magnesium stearate.

Preferably, in step S5, the amisulpride tablet has a hardness of 50 N to 80 N.

The present disclosure has following beneficial effects:

In the present disclosure, a brand new solution is provided for a sticking problem caused by inherent properties of the amisulpride. The amisulpride is coated with a polymer coating material, and then the coated granules are mixed with a highly hydrophilic lubricant. The preparation method avoids easy sticking of the amisulpride. Meanwhile, the prepared amisulpride tablet has high hardness and desirable dissolution rate.

BRIEF DESCRIPTION OF THE DRAWINGS

FIG. 1A is a sticking photo during the compressing of Example 1 in the present disclosure; and FIG. 1B is a sticking photo during the compressing of Comparative Example 1 in the present disclosure.

DETAILED DESCRIPTION OF THE EMBODIMENTS

Figure 1A:
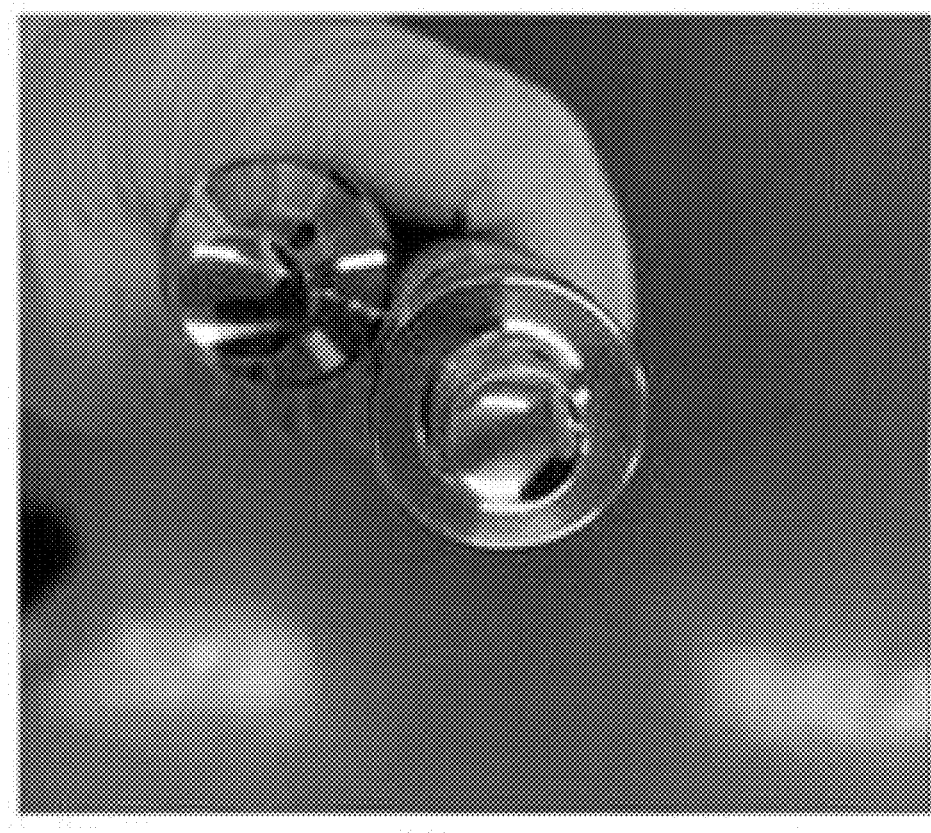
FIG. 1A and FIG. 1B show sticking photos of amisulpride during the compressing, specifically.

The below description of examples is merely provided to help understand the method of the present disclosure and a core idea thereof. It should be noted that several improvements and modifications may be made by persons of ordinary skill in the art without departing from the principle of the present disclosure, and these improvements and modifications should also fall within the protection scope of the present disclosure. The below description of the disclosed embodiments enables those skilled in the art to achieve or use the present disclosure. Various modifications to these embodiments are readily apparent to those skilled in the art, and the generic principles defined herein may be practiced in other embodiments without departing from the spirit or scope of the present disclosure. Therefore, the present disclosure is not limited to the examples shown herein but falls within the widest scope consistent with the principles and novel features disclosed herein. Although any methods and materials similar or equivalent to those described herein can be used in the practice or testing of the present disclosure, the preferred methods and materials are described herein.

Unless otherwise specified, all technical and scientific terms used herein have the same meanings as those generally understood by those of ordinary skill in the art to which the present disclosure pertains.

Example 1 A Preparation Method of an Amisulpride Tablet

The prescription information of the amisulpride tablet was shown in Table 1.

TABLE 1

| Prescription dosage of amisulpride tablet | | | |
|---|---|---|---|
| SN | Component | Effect | Prescription ratio/g |
| 1 | Amisulpride | Active ingredient | 46 |
| 2 | Ethyl cellulose | Coating material | 1 |
| 3 | HPC | Coating material | 1 |
| 4 | crospovidone | Disintegrant | 7 |
| 5 | magnesium stearate | Lubricant | 0.8 |
| 6 | Sweet orange powder flavor | Flavoring agent | 0.7 |
| 7 | MCC | Filler | 10 |
| 8 | Mannitol | Filler | 30 |
| 9 | Sucralose | Sweetener | 2.5 |
| 10 | Sodium stearyl fumarate | Lubricant | 1 |

The preparation method included:

(1) Preparation of a coating material: a coating material was formulated with 95% ethanol to form a coating material with a concentration of 5%.

(2) Wet granulation: a prescribed amount of amisulpride was added in a wet granulator, ¼ of the coating material was added by spraying, and the wet granulation was conducted to obtain wet granules.

(3) Coating: the wet granules were coated in a fluidized bed using a fluidized bed top spraying process, and all coating materials were sprayed in and dried until a weight loss on drying was less than 3%, and then the drying was stopped.

(4) Sieving: after the coating was completed, a coated material was passed through a 1.0 mm mesh plate by a rapid sieving machine, to obtain coated granules.

(5) First mixing: a prescribed amount of sodium stearyl fumarate was added into the coated granules, and mixed for 10 min to obtain a material 1.

(6) Second mixing: other auxiliary materials in the prescription except magnesium stearate were added to the material 1, and mixed for 15 min to obtain material 2.

(7) Total mixing: a prescribed amount of the magnesium stearate was added to the material 2, and mixed for 5 min to obtain a total mixture.

(8) Compressing: the total mixture was compressed to obtain a tablet with a hardness of 80 N.

Example 2 A Preparation Method of an
Amisulpride Tablet

The prescription information of the amisulpride tablet was shown in Table 2.

TABLE 2

Prescription dosage of amisulpride tablet

| SN | Component | Effect | Prescription ratio/g |
|----|-----------|--------|----------------------|
| 1 | Amisulpride | Active ingredient | 36 |
| 2 | Ethyl cellulose | Coating material | 0.5 |
| 3 | HPC | Coating material | 0.5 |
| 4 | crospovidone | Disintegrant | 5.5 |
| 5 | magnesium stearate | Lubricant | 1.5 |
| 6 | Sweet orange powder flavor | Flavoring agent | 1.5 |
| 7 | MCC | Filler | 15 |
| 8 | Mannitol | Filler | 35 |
| 9 | Sucralose | Sweetener | 3 |
| 10 | Sodium stearyl fumarate | Lubricant | 1.5 |

The preparation method included:
(1) Preparation of a coating material: a coating material was formulated with 95% ethanol to form a coating material with a concentration of 5%.
(2) Wet granulation: a prescribed amount of amisulpride was added in a wet granulator, $\frac{1}{5}$ of the coating material was added by spraying, and the wet granulation was conducted to obtain wet granules.
(3) Coating: the wet granules were coated in a fluidized bed using a fluidized bed top spraying process, and all coating materials were sprayed in and dried until a weight loss on drying was less than 3%, and then the drying was stopped.
(4) Sieving: after the coating was completed, a coated material was passed through a 1.0 mm mesh plate by a rapid sieving machine, to obtain coated granules.
(5) First mixing: a prescribed amount of sodium stearyl fumarate was added into the coated granules, and mixed for 10 min to obtain a material 1.
(6) Second mixing: other auxiliary materials in the prescription except magnesium stearate were added to the material 1, and mixed for 15 min to obtain material 2.
(7) Total mixing: a prescribed amount of the magnesium stearate was added to the material 2, and mixed for 5 min to obtain a total mixture.
(8) Compressing: the total mixture was compressed to obtain a tablet with a hardness of 52 N.

Example 3 A Preparation Method of an
Amisulpride Tablet

The prescription information of the amisulpride tablet was shown in Table 3.

TABLE 3

Prescription dosage of amisulpride tablet

| SN | Component | Effect | Prescription ratio/g |
|----|-----------|--------|----------------------|
| 1 | Amisulpride | Active ingredient | 54 |
| 2 | Ethyl cellulose | Coating material | 1.5 |
| 3 | HPC | Coating material | 1.5 |
| 4 | crospovidone | Disintegrant | 10 |
| 5 | magnesium stearate | Lubricant | 0.5 |
| 6 | Sweet orange powder flavor | Flavoring agent | 0.1 |

TABLE 3-continued

Prescription dosage of amisulpride tablet

| SN | Component | Effect | Prescription ratio/g |
|----|-----------|--------|----------------------|
| 7 | MCC | Filler | 5 |
| 8 | Mannitol | Filler | 25 |
| 9 | Sucralose | Sweetener | 1.9 |
| 10 | Sodium stearyl fumarate | Lubricant | 0.5 |

The preparation method included:
(1) Preparation of a coating material: a coating material was formulated with 95% ethanol to form a coating material with a concentration of 5%.
(2) Wet granulation: a prescribed amount of amisulpride was added in a wet granulator, $\frac{3}{10}$ of the coating material was added by spraying, and the wet granulation was conducted to obtain wet granules.
(3) Coating: the wet granules were coated in a fluidized bed using a fluidized bed top spraying process, and all coating materials were sprayed in and dried until a weight loss on drying was less than 3%, and then the drying was stopped.
(4) Sieving: after the coating was completed, a coated material was passed through a 1.0 mm mesh plate by a rapid sieving machine, to obtain coated granules.
(5) First mixing: a prescribed amount of sodium stearyl fumarate was added into the coated granules, and mixed for 10 min to obtain a material 1.
(6) Second mixing: other auxiliary materials in the prescription except magnesium stearate were added to the material 1, and mixed for 15 min to obtain material 2.
(7) Total mixing: a prescribed amount of the magnesium stearate was added to the material 2, and mixed for 5 min to obtain a total mixture.
(8) Compressing: the total mixture was compressed to obtain a tablet with a hardness of 66 N.

Comparative Example 1 A Preparation Method of
an Amisulpride Tablet

This comparative example differed from Example 1 in that the preparation method included:
(1) Preparation of a coating material: a coating material was formulated with 95% ethanol to form a coating material with a concentration of 5%.
(2) Wet granulation: a prescribed amount of amisulpride was added in a wet granulator, the coating material was added by spraying, and the wet granulation was conducted to obtain wet granules.
(3) Coating: the wet granules were coated in a fluidized bed using a fluidized bed top spraying process, and all coating materials were sprayed in and dried until a weight loss on drying was less than 3%, and then the drying was stopped.
(4) Sieving: after the coating was completed, a coated material was passed through a 1.0 mm mesh plate by a rapid sieving machine, to obtain coated granules.
(5) mixing: other auxiliary materials in the prescription except magnesium stearate were mixed with the coated granules for 30 min to obtain a material.
(6) Total mixing: a prescribed amount of the magnesium stearate was added to the material, and mixed for 5 min to obtain a total mixture.

(7) Compressing: the total mixture was compressed to obtain a tablet with a hardness of 78N.

Comparative Example 2 A Preparation Method of an Amisulpride Tablet

This comparative example differed from Example 1 in that the prescription information of the amisulpride tablet was shown in Table 4, and the amisulpride tablet prepared therefrom had a hardness of 36 N.

TABLE 4

| | Prescription dosage of amisulpride tablet | | |
|---|---|---|---|
| SN | Component | Effect | Prescription ratio/g |
| 1 | Amisulpride | Active ingredient | 46 |
| 2 | Ethyl cellulose | Coating material | 3.5 |
| 3 | HPC | Coating material | 0 |
| 4 | crospovidone | Disintegrant | 7 |
| 5 | magnesium stearate | Lubricant | 1.8 |
| 6 | Sweet orange powder flavor | Flavoring agent | 0.7 |
| 7 | MCC | Filler | 10 |
| 8 | Mannitol | Filler | 30 |
| 9 | Sucralose | Sweetener | 2.5 |
| 10 | Sodium stearyl fumarate | Lubricant | 1 |

Comparative Example 3 A Preparation Method of an Amisulpride Tablet

This comparative example differed from Example 1 in that the prescription information of the amisulpride tablet was shown in Table 5, and the amisulpride tablet prepared therefrom had a hardness of 72 N.

TABLE 5

| | Prescription dosage of amisulpride tablet | | |
|---|---|---|---|
| SN | Component | Effect | Prescription ratio/g |
| 1 | Amisulpride | Active ingredient | 46 |
| 2 | Ethyl cellulose | Coating material | 1 |
| 3 | HPC | Coating material | 1 |
| 4 | crospovidone | Disintegrant | 7 |
| 5 | magnesium stearate | Lubricant | 0.2 |
| 6 | Sweet orange powder flavor | Flavoring agent | 0.7 |
| 7 | MCC | Filler | 10 |
| 8 | Mannitol | Filler | 30 |

TABLE 5-continued

| | Prescription dosage of amisulpride tablet | | |
|---|---|---|---|
| SN | Component | Effect | Prescription ratio/g |
| 9 | Sucralose | Sweetener | 2.5 |
| 10 | Sodium stearyl fumarate | Lubricant | 1.6 |

I. Sticking and Hardness

TABLE 6

| Anti-sticking and tablet hardness of examples and comparative examples | | |
|---|---|---|
| Group | Sticking (yes or no) | Tablet hardness/N |
| Example 1 | No | 80 |
| Example 2 | No | 52 |
| Example 3 | No | 66 |
| Comparative Example 1 | Yes | 78 |
| Comparative Example 2 | No | 36 |
| Comparative Example 3 | No | 72 |

As shown in Table 6, in the present disclosure, the amisulpride was coated with the coating material, and then the hydrophilic lubricant was mixed with the coated granules. This effectively avoided the sticking of amisulpride during the compressing, as shown in FIG. 1A. Simultaneously, it was seen from Examples 1 to 3 that the amisulpride tablet had a relatively high hardness of 50 N to 80 N.

Figure 1B:
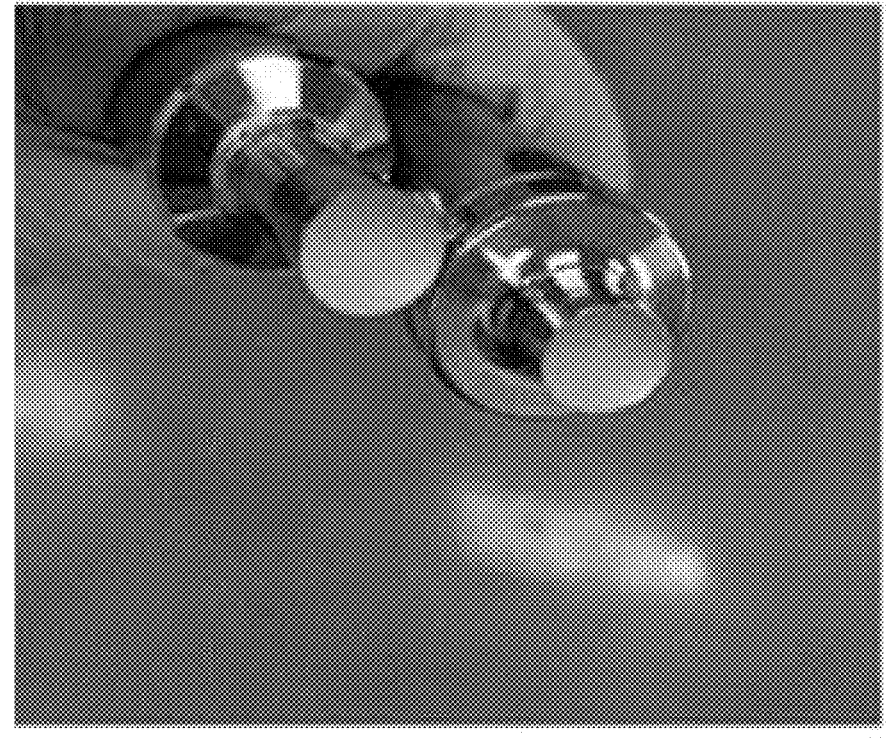

Compared with Example 1, the preparation method was changed in Comparative Example 1, and the amisulpride was coated with the coating material, and then mixed with other auxiliary materials not containing the hydrophobic lubricant. The prepared tablet had a high hardness of 78 N, but there was still obvious sticking of amisulpride during the compressing, as shown in FIG. 1B.

In Comparative Examples 2 and 3, the dosages of the coating material, hydrophilic lubricant, and hydrophobic lubricant were changed. The amisulpride did not have sticking during the compressing, but the tablet prepared in Comparative Example 2 had a lower hardness.

II. Dissolution Rate Testing

The dissolution rate test results of the amisulpride tablet obtained by the preparation method of the present disclosure were all consistent with those of a reference preparation, and could be dissolved very quickly. That is, the newly added formulation and process did not affect the release of the product. A result was as follows:

The dissolution test results of a pH=1.0 medium were shown in Table 7.

TABLE 7

| Dissolution test results of pH = 1.0 medium | | | | | | | | | | | | | |
|---|---|---|---|---|---|---|---|---|---|---|---|---|---|
| | pH = 1.0 medium | | | | | | | | | | | | |
| | Control preparation | | Example 1 | | Example 2 | | Example 3 | | Comparative Example 2 | | Comparative Example 3 | | |
| Time/ min | Mean % | RSD % | Mean % | RSD % | Mean % | RSD % | Mean % | RSD % | Mean % | RSD % | Mean % | RSD % | |
| 0 | 0 | 0 | 0 | 0 | 0 | 0 | 0 | 0 | 0 | 0 | 0 | 0 | |
| 5 | 69 | 14.7 | 97 | 0.5 | 95 | 0.7 | 96 | 0.6 | 62 | 12.5 | 48 | 16.2 | |
| 10 | 97 | 2.8 | 99 | 0.4 | 99 | 0.3 | 99 | 0.3 | 86 | 8.0 | 86 | 10.4 | |
| 15 | 100 | 1.4 | 100 | 0.3 | 100 | 0.5 | 100 | 0.5 | 91 | 3.2 | 92 | 1.8 | |
| 30 | 101 | 1.3 | 100 | 0.3 | 100 | 0.5 | 101 | 0.5 | 100 | 2.0 | 92 | 1.7 | |
| 45 | 102 | 1.3 | 101 | 0.3 | 100 | 0.5 | 101 | 0.5 | 100 | 2.0 | 93 | 1.7 | |

The medium was hydrochloric acid, the dissolution rate test was conducted at 37° C.±0.5° C., and a rotational speed was 50 rpm.

The dissolution test results of a pH=4.5 medium were shown in Table 8.

TABLE 8

| | Dissolution test results of pH = 4.5 medium | | | | | | | | | | | |
| | | | | | | | | | | | | |
| | | pH = 4.5 medium | | | | | | | | | | |
| | Control preparation | | Example 1 | | Example 2 | | Example 3 | | Comparative Example 2 | | Comparative Example 3 | |
| Time/ min | Mean % | RSD % | Mean % | RSD % | Mean % | RSD % | Mean % | RSD % | Mean % | RSD % | Mean % | RSD % |
|---|---|---|---|---|---|---|---|---|---|---|---|---|
| 0 | 0 | 0 | 0 | 0 | 0 | 0 | 0 | 0 | 0 | 0 | 0 | 0 |
| 5 | 73 | 2.6 | 91 | 1.3 | 89 | 1.5 | 91 | 1.2 | 60 | 2.7 | 56 | 3.0 |
| 10 | 96 | 1.7 | 97 | 1.1 | 95 | 1.2 | 96 | 1.5 | 85 | 2.2 | 70 | 2.8 |
| 15 | 98 | 1.6 | 98 | 1.4 | 97 | 1.7 | 98 | 1.1 | 90 | 2.0 | 87 | 2.6 |
| 30 | 98 | 1.3 | 99 | 1.3 | 99 | 1.3 | 99 | 1.2 | 92 | 1.6 | 90 | 1.9 |
| 45 | 99 | 1.4 | 100 | 1.1 | 100 | 1.2 | 100 | 1.1 | 94 | 1.2 | 91 | 1.8 |

The medium was an acetate buffer, the dissolution rate test was conducted at 37° C.±0.5° C., and a rotational speed was 50 rpm.

The dissolution test results of a pH=6.8 medium were shown in Table 9.

TABLE 9

| | Dissolution test results of pH = 6.8 medium | | | | | | | | | | | |
| | | | | | | | | | | | | |
| | | pH = 6.8 medium | | | | | | | | | | |
| | Control preparation | | Example 1 | | Example 2 | | Example 3 | | Comparative Example 2 | | Comparative Example 3 | |
| Time/ min | Mean % | RSD % | Mean % | RSD % | Mean % | RSD % | Mean % | RSD % | Mean % | RSD % | Mean % | RSD % |
|---|---|---|---|---|---|---|---|---|---|---|---|---|
| 0 | 0 | 0 | 0 | 0 | 0 | 0 | 0 | 0 | 0 | 0 | 0 | 0 |
| 5 | 51 | 26.7 | 83 | 2.3 | 80 | 2.5 | 85 | 2.2 | 48 | 24.8 | 36 | 27.1 |
| 10 | 94 | 2.9 | 93 | 1.9 | 91 | 2.1 | 94 | 1.9 | 90 | 5.6 | 87 | 7.6 |
| 15 | 97 | 1.3 | 98 | 1.4 | 97 | 1.7 | 97 | 1.6 | 92 | 2.8 | 90 | 3.0 |
| 30 | 98 | 1.1 | 100 | 0.8 | 100 | 1.0 | 100 | 0.9 | 93 | 2.5 | 90 | 2.9 |
| 45 | 98 | 1.0 | 100 | 0.8 | 100 | 0.9 | 100 | 0.9 | 93 | 2.4 | 91 | 2.6 |

The medium was PBS, the dissolution rate test was conducted at 37° C.±0.5° C., and a rotational speed was 50 rpm.

The above is a further description of the present disclosure in conjunction with specific examples, but the examples are only exemplary and do not constitute any limitation on the scope of the present disclosure. Those skilled in the art will appreciate that modifications and substitutions of the technical solutions of the present disclosure can be made in form and detail without departing from the spirit and scope of the present disclosure, but all of these modifications and substitutions fall within the protection scope of the present disclosure.

What is claimed is:

1. A preparation method of an amisulpride tablet, comprising the following steps:
S1, granulation: conducting wet granulation on amisulpride with a coating material to obtain wet granules; wherein the coating material comprises ethyl cellulose and hydroxypropyl cellulose at a mass ratio of 1:1;
S2, coating: subjecting the wet granules obtained in step S1 to coating with additional coating material, drying, and sieving to obtain coated granules; wherein the additional coating material comprises the ethyl cellulose and the hydroxypropyl cellulose at a mass ratio of 1:1;

S3, first mixing: mixing the coated granules obtained in step S2 with a hydrophilic lubricant to obtain a material 1; wherein the hydrophilic lubricant is sodium stearyl fumarate, and is added at 0.5% to 1.5% of the weight of the amisulpride tablet;

S4, second mixing: adding an auxiliary material into the material 1 obtained in step S3, and mixing to obtain a material 2; wherein the auxiliary material comprises at least one of a disintegrant, a filler, a sweetener, or a flavoring agent, and does not comprise a lubricant;

S5, total mixing: mixing the material 2 obtained in step S4 with a hydrophobic lubricant to obtain a total mixture; wherein the hydrophobic lubricant is magnesium stearate, and accounts for 0.5% to 1.5% of the weight of the amisulpride tablet; and S6, compressing: compressing the total mixture obtained in step S5 to obtain the amisulpride tablet.

2. The preparation method according to claim 1, wherein a total amount of the coating material and the additional coating material is 1% to 3% of the weight of the amisulpride tablet.

3. The preparation method according to claim 2, wherein the coating material in step S1 accounts for 20% to 30% of a total mass of the coating material and the additional coating material.

* * * * *